US005834442A

United States Patent [19]
Raz et al.

[11] Patent Number: 5,834,442
[45] Date of Patent: Nov. 10, 1998

[54] METHOD FOR INHIBITING CANCER METASTASIS BY ORAL ADMINISTRATION OF SOLUBLE MODIFIED CITRUS PECTIN

[75] Inventors: Avraham Raz, West Bloomfield; Kenneth J. Pienta, Troy, both of Mich.

[73] Assignees: Barbara Ann Karmanos Cancer Institute; Wayne State University, Detroit, both of Mich.

[21] Appl. No.: 271,821

[22] Filed: Jul. 7, 1994

[51] Int. Cl.$^6$ .................................... A61K 31/725
[52] U.S. Cl. ................................................. 514/54
[58] Field of Search ...................... 514/310, 54

[56] References Cited

U.S. PATENT DOCUMENTS

| | | | |
|---|---|---|---|
| 4,241,099 | 12/1980 | Tiemstra | 426/577 |
| 4,264,592 | 4/1981 | Xhanjanka | 424/195 |
| 4,689,322 | 8/1987 | Kulbe et al. | 514/54 |
| 4,904,697 | 2/1990 | Sunkara et al. | 514/629 |
| 4,950,655 | 8/1990 | Bachmann | 514/54 |
| 4,959,227 | 9/1990 | Amer | 426/35 |
| 4,988,530 | 1/1991 | Hoersten et al. | 426/577 |
| 5,374,444 | 12/1994 | Langner | 426/590 |
| 5,441,943 | 8/1995 | McAnalley et al. | 514/54 |

OTHER PUBLICATIONS

J. Raloff, "Jamming Prostate Cancer's Transmission", Science News, vol. 147, p. 134, Mar. 1995.

Pienta et al., "Inhibition . . . Citrus Pectin", J. Of the Nat. Cancer Inst., vol. 87, No. 5, pp. 348–353, Mar. 1995.

"Inhibition of Spontaneous Rat Prostate Cancer By Oral Administration of Modified Citrus Pectin"; Pienta et al., J. Nat'l Cancer Institute, Mar. 1, 1995, 87(5), 348–53.

"Effects of Natural Complex Carbohydrate (Citrus Pectin) On Murine Melanoma Cell Properties Related to Galectin–3 Functions"; Inohara et al.; Glycocon J, Dec. 1994, 11(6), pp. 527–532.

"Modulation of the lung colonization of B16–F1 melanoma cells by citrus pectin," by Platt, D., and Raz, A., J. Natl Cancer Inst, Mar. 18, 1992, 84 (6), P438–42.

Abstract, "Modified Pectin".

Platt et al., "Modulation . . . Citrus Pectin", J. Natl. Cancer Inst., vol. 84, No. 6, pp. 438–442, Mar. 1992.

Platt et al., "Modulation of the Lung Colonization of B16–F1 Melanoma Cells by Citrus Pectin", J. Natl., Cancer Inst., vol. 84, No. 5, pp. 438–442, Mar. 1992.

*Primary Examiner*—José G. Dees
*Assistant Examiner*—Rosalynd Williams
*Attorney, Agent, or Firm*—Dykema Gossett PLLC

[57] ABSTRACT

A method for the treatment of cancer in mammals. A subject afflicted with cancer receives by oral administration a pH modified citrus pectin which inhibits metastasis of primary tumors.

2 Claims, 7 Drawing Sheets

METHOD FOR INHIBITING CANCER METASTASIS BY ORAL ADMINISTRATION OF SOLUBLE MODIFIED CITRUS PECTIN

This invention was made with Government support, under Contract No. R01 CA 57453, awarded by the National Institute of Health. The Government has certain rights in the invention.

FIELD OF THE INVENTION

The present invention relates generally to methods for treating prostate cancer.

BACKGROUND OF THE INVENTION

The incidence of many forms of cancer is expected to increase as the population ages. For example, prostate cancer is the most commonly diagnosed cancer in United States men as well as the second leading cause of male cancer deaths. It is projected that in 1994 there will be 200,000 new cases of prostate cancer diagnosed as well as 38,000 deaths from prostate cancer and these numbers are expected to continue to rise as the population ages. Approximately 50% of patients diagnosed with prostate cancer have disease which has or will escape the prostate. Prostate cancer metastasizes to the skeletal system and patients typically die with overwhelming osseous metastatic disease. As yet, there is no effective curative therapy and very little palliative therapy for patients with metastatic disease.

The process of tumor cell metastasis requires that cells depart from the primary tumor, invade the basement membrane, traverse through the bloodstream from tumor cell emboli, interact with the vascular endothelium of the target organ, extravasate, and proliferate to form secondary tumor colonies as described by E. C. Kohn, Anticancer Re., 13, 2553 (1993); and L. A. Kiotta, P. S. Steeg, W. G. Stettler-Stevenson, Cell 64, 327 (1991).

It is generally accepted that many stages of the metastatic cascade involve cellular interactions mediated by cell surface components such as carbohydrate-binding proteins, which include galactoside binding lectins (galectins) as described by A. Raz, R. Lotan, Cancer Metastasis Rev. 6, 433 (1987); and H. J. Gabius, Biochim Biophys Acta 1071, 1 (1991). Treatment of B16 melanoma and uv-2237 fibrosarcoma cells in vitro with anti-galectin monoclonal antibodies prior to their intravenous (i.v.) injection into the tail vein of syngeneic mice resulted in a marked inhibition of tumor lung colony development as described by L. Meromsky, R. Lotan, A. Raz, Cancer Res. 46, 5270 (1991). Transfection of low metastatic, low galectin-3 expressing uv-2237-c115 fibrosarcoma cells with galectin-3 cDNA resulted in an increase of the metastatic phenotype of the transfected cells as described by A. Raz, D. Zhu, V. Hogan, J. Shah, T. Raz, R. Karkash, G. Pazerini, P. Carmi, Int. J Cancer 46, 871 (1990). Furthermore, a correlation has been established between the level of galectin-3 expression in human papillary thyroid carcinoma and tumor stage of human colorectal and gastric carcinomas as described by L. Chiariotti, M. T. Berlinjieri, P. DeRosa, C. Battaglia, N. Berger, C. B. Bruni, A. Fusco, Omeogene 7, 2507 (1992); L. Irimura, Y. Matsushite, R. C. Sutton, D. Carralero, D. W. Ohanesian, K. R. Cleary, D. M. Ota, Int J Cancer 51, 387 (1991); R. Lotan, H. Ito, W. Yasui, H. Yokozak, D. Lotan, E. Tahara, Int J Cancer 56, 474 (1994); and M. M. Lotz, C. W. Andrews, C. A. Korzelius, E. C. Lee, G. D. Steele, A. Clarke, A. M. Mercurio, PNAS, U.S.A. 90, 3466 (1993).

Simple sugars such as methyl-alpha-D lactoside and lacto-N-tetrose have been shown to inhibit metastasis of B16 melanoma cells, while D-galactose and arabinogalactose inhibited liver metastasis of L-1 sarcoma cells as described by J. Beauth et al., J Cancer Res Clin Oncol 113, 51 (1987).

It is known that intravenous injection of B16-F1 murine melanoma cells with citrus pectin or modified citrus pectin into syngenic mice resulted in a significant increase or decrease of lung colonization, respectfully as described by D. Platt and A. Raz, J. Natl Cancer Inst. 84:438–42 (1992). Prior to the discovery disclosed herein, an effective treatment for inhibiting cancer metastasis utilizing a non-cytotoxic agent by oral administration did not exist. Thus, a need exists for a therapy which is based on the oral administration of an non-cytotoxic agent.

SUMMARY OF INVENTION

In one aspect, the present invention provides a method of treating cancer in mammals by the oral administration of modified pectin, preferably water soluble pH modified citrus pectin, as described herein to inhibit metastasis.

In another aspect, the present invention provides a composition for the treatment of cancer in mammals which comprises a mixture of modified pectin, preferably pH modified citrus pectin, and a pharmaceutically acceptable digestible carrier for oral administration.

In still another aspect, the method and compositions of the present invention are utilized in the therapeutic treatment of prostate cancer in man and other mammals to inhibit metastasis of primary tumors.

Accordingly, the preferred embodiment the present invention provides a novel therapy in which oral intake of a non-cytotoxic natural complex carbohydrate rich in galactoside residues, i.e., pH-modified citrus pectin (MCP), acts as a potent inhibitor of spontaneous prostate carcinoma metastasis.

When treated in accordance with the present invention, 7 out of 16 tumor bearing rats were observed to be disease-free at autopsy (no visible metastases in lymph nodes or lungs) following removal of the primary tumor at day 14 after the inoculation of $10^6$ Dunning rat prostate adenocarcinoma MLL cells while 16/16 of the rats in the control group had metastases. The number of tumor lung colonies in the remaining animals was markedly reduced by oral intake of 1% (w/v) MCP as compared with the control group (control, 9±4; 1% MCP, 1±1), with no effect on the growth of the primary tumors. In vitro, MCP inhibited MLL cell adhesion to rat endothelial cells in a time and dose dependent manner as well as their colony formation in semi-solid medium. The possible mechanism of action of MCP appears to involve tumor cell surface carbohydrate-binding proteins.

Thus, the present invention provides a method for the treatment of cancer by the oral administration of MCP, a non-toxic drug with a unique mechanism of action that results in the successful inhibition of tumor cell dissemination. In addition, the present invention provides a composition for the treatment of mammalian cancer comprising MCP in combination with an oral pharmaceutical carrier.

DETAILED DESCRIPTION OF THE PREFERRED EMBODIMENTS

Figure 1A:
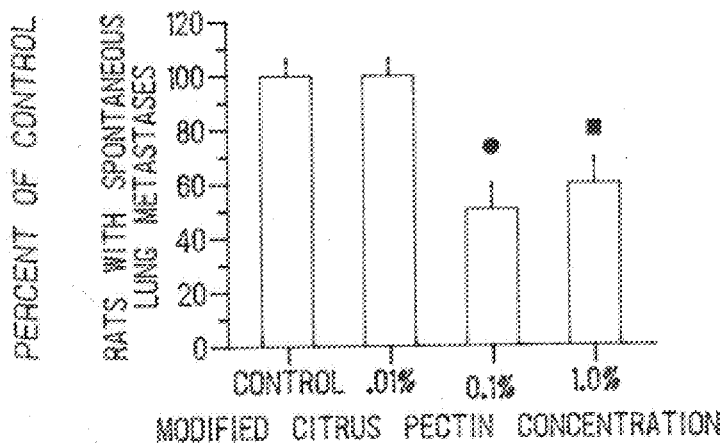
FIG. 1A is a chart which illustrates that the number of rats which suffered lung metastases was significantly reduced compared to control in the 0.1% MCP and the 1.0% MCP.

As used herein, the term "therapeutic" treatment refers to oral administration of a predetermined amount of modified citrus pectin to a subject after the subject has been diagnosed as having cancer which is effective for increased survival of the subject.

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer. Preferably, the cancer which is treated in the present invention is human prostate cancer, most preferably adenocarcinoma of the human prostate.

The abbreviations used herein are: CP, natural citrus pectin; MCP, pH-modified CP; EHS, Englebreth-Holm Swarm; DMEM, Dulbecco's modified Eagle's minimal essential medium; CMF-PBS, $Ca^{2+}$- and $MG^{2+}$-free phosphate-buffered saline, pH 7.2; BSa, bovine serum albumin.

Previously, the effect of citrus pectin (CP), a complex polysaccharide rich in galactosyl residues, and its pH-modified derivative (MCP) on the experimental metastasis of B16 melanoma was analyzed as described in the article, Modulation of the Lung Colonization of B16-F1 Melanoma Cells by Citrus Pectin, Journal of the National Cancer Institute, Vol. 84, No. 6, Mar. 18, 1992, the entire disclosure of which is incorporated herein by reference. It was found that co-injection of MCP with the B16-F1 cells intravenously resulted in a marked inhibition of their ability to colonize the lungs of the injected mice. pH modification of CP, as will be described more fully hereinafter, results in the generation of smaller sized non-branched carbohydrate chains of similar sugar composition of the unmodified CP. MCP appears to be non-toxic, in vitro and in vivo.

The modified pectin utilized in the present invention is prepared by partially depolymerizing citrus pectin, preferably by pH modification.

As will be understood by those skilled in the art, unmodified pectin has a molecular weight range of between about 20,000–400,000. It is a polysaccharide substance present in cell walls of all plant tissues which functions as an intercellular cementing material. One of the richest sources of pectin is lemon or orange rind which contains about 30% of this polysaccharide. It occurs naturally as the partial methyl ester of $_a$_(1_4) linked D-polygalacturonate sequences interrupted with (1_2)-L-rhamnose residues. The neutral sugars, D-galactose, L-arabinose, D-xylose and L-fucose form side chains on the pectin molecule. Structure studies were made by D. A. Rees, A. W. Wight, *J. Chem. Soc. B*, 1971, 1366. Secondary and tertiary structure in solution and in gels is described in D. A. Rees, E. J. Welsh, *Angew. Chem. Int. Ed.* 16, 214 (1977). A review and bibliography is set forth by Towle, Christensen, in *Industrial Gums*, R. L. Whistler, Ed. (Academic Press, New York, 2nd ed., 1973) p. 429–461. One noteworthy book on pectins is by Z. I. Kertesz, *The Pectic Substances* (Interscience, New York, 1951).

Pectin occurs as a coarse or fine powder, yellowish-white in color, practically odorless, and with a mucilaginous taste. It is almost completely soluble in 20 parts water, forming a viscous solution containing negatively charged, very much hydrated particles. It is acid to litmus and insoluble in alcohol or in diluted alcohol, and in other organic solvents. It dissolves more readily in water, if first moistened with alcohol, glycerol or sugar syrup, or if first mixed with 3 or more parts of sucrose. It is stable under mildly acidic conditions; more strongly acidic or basic conditions cause depolymerization.

One preferred pectin for use as a starting material in the preparation of pH modified citrus pectin for use in the present invention can be obtained from Sigma Chemical Co. of St. Louis, Mo. This material has a molecular mass of 70–100 kd, is approximately 85% by weight galacturonic and 9.5% by weight methoxyl groups and containing less than approximately 10% by weight moisture. It is available as a powder. Citrus pectin is also available from ICN Biomedicals as Pectin 102587 RT.

A 0.5% and more preferably, a 1.0% w/v aqueous solution (all solution concentration herein are expressed as w/v unless otherwise indicated) of the citrus pectin is prepared and sterilized under UV radiation for about 48 hours. In order to partially depolymerize the pectin, the pectin solution is modified by increasing the pH to 10.0 with NaOH (3N) for 30 minutes and then decreasing the pH to 3.0 with HCl (3N) according to the method described by Alberscheim et al., in the article, "A Method for Analysis of Sugars in Plant Cell Wall Polysaccharides by Gas Liquid Chromatography", Carbohydrate Research, 5:340–346, 1967, the entire disclosure of which is incorporated herein by reference. After about 10 to 24 hours, the pH of the solution is equilibrated to about 6.3. The solution is then washed with ethanol (70%) and dried with acetone (100%). This results in pectin fragments having an average molecular mass of about 10 kd as determined by viscosity measurements at 25 C in a Ubbelohde No. 1 viscometer with sodium-hexametalphosphate at 20 mM (pH 4.5), 0.2% EDTA and (0.9%) NaCl according to the method of Christensen in the article, "Methods of Grading Pectin in Relation to the Molecular Weight (intrinsic viscosity of pectin)", Food Research 19:163–165 (1954), the entire disclosure of which is incorporated herein by reference. As used herein, the terms "modified pectin" and "MCP" shall refer to depolymerized pectin. More preferably, the modified pectin utilized in the present invention has a molecular mass of from about 1–15 kd and most preferably about 10 kd and is preferably prepared in accordance with the protocol set forth above and is preferably water soluble. The dried MCP fragments may then be rehydrated with $Ca^{2+}$ and $Mg^{2+}$-free phosphate-buffered saline (pH 7.2) (CMF-PBS) to a final stock solution of 0.5% (w/v).

As stated, in the present invention, MCP is administered orally and therefore the present invention provides a composition which contains MCP and a digestible pharmaceutical carrier. Suitable digestible pharmaceutical carriers include gelatin capsules in which the MCP is encapsulated in dry form, or tablets in which MCP is admixed with hydroxyporoyl cellulose, hydroxypropyl methylcellulose, magnesium stearate, microcrystalline cellulose, propylene glycol, zinc stearate and titanium dioxide and the like. The composition may be formulated as a liquid using purified water, flavoring agents and sucrose as a digestible carrier to make a pleasant tasting composition when consumed by the subject.

The precise dose and dosage regimen is a function of variables such as the subject's age, weight, medical history and the like. The preferred dose and dosage regimen based on the weight of the MCP component (i.e., disregarding the digestible carrier) effective in the treatment of cancer is a daily dose of about 10 to about 1000 mg per kg of body weight of the subject. The MCP is administered orally at equal intervals i.e., from about 10 to about 1000 mg/kg every 24 hours and/or 2.5 to 250 mg/Kg every 6 hours. This same dosage and dosage regimen is preferred for use in the treatment of prostate cancer in mammals, including human prostate cancer, to reduce or inhibit metastasis. It is believed that this same dose and dosage regimen will be effective in the prevention of cancer in high risk mammalian subjects when administered as an oral prophylactic composition.

EXAMPLES

The various aspects of the invention are further described by the following examples, which are not intended to limit the invention in any manner.

The Dunning (R3327) rat prostate adenocarcinoma model of prostate cancer was developed by Dunning from a spontaneously occurring adenocarcinoma found in a male rat as described by W. F. Dunning, Natl Cancer Inst Mono 12, 351 (1963). Several sublines have been developed from the primary tumor which have varying differentiation and metastatic properties as described by J. T. Isaacs, W. D. W. Heston, R. M. Weissman, D. S. Coffey, Cancer Res 38, 4353 (1978). The MAT-LyLu (MLL) subline is a fast growing, poorly differentiated adenocarcinoma cell line which upon injection of $1 \times 10^6$ MLL cells into the thigh of the rat leads to animal death within approximately 25 days secondary to overwhelming primary tumor burden as described by J. T. Isaacs, W. B. Isaacs, W. F. J. Feitz, J. Scheres, The Prostate 9, 261 (1986); and K. J. Pienta, B. C. Murphy, W. B. Isaacs, J. T. Isaacs, D. S. Coffey, The Prostate 20, 233 (1992). The primary MLL tumor starts to metastasize approximately 12 days after tumor cell inoculation and removal of the primary tumor by limb amputation prior to this time results in animal cure. If amputation is performed after day 12, most of the animals die of lung and lymph node metastases within 40 days as described by K. J. Pienta, B. C. Murphy, W. B. Isaacs, J. T. Isaacs, D. S. Coffey, The Prostate 20, 233 (1992).

In the present invention, soluble MCP, given orally in the drinking water on a chronic basis, affects the ability of the MLL tumor to establish spontaneous metastases.

Figure 1B:
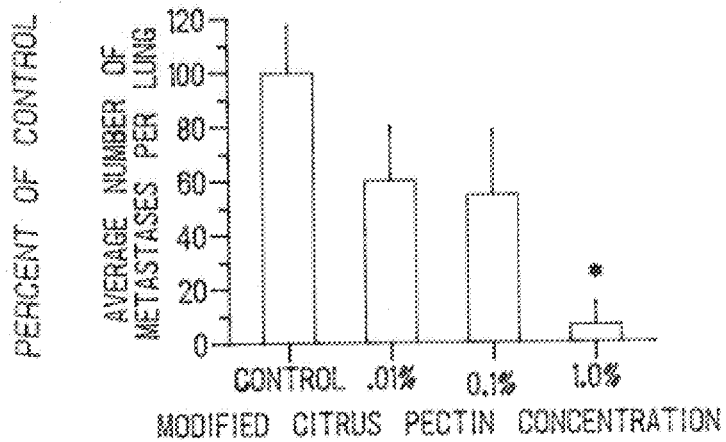
FIG. 1B is a chart which illustrates that the lungs of the 1.0% MCP treated animals had significantly fewer metastatic colonies than control groups.
Figure 1C:
FIG. 1C is a photomicrograph of lungs of control rats.
Figure 1D:
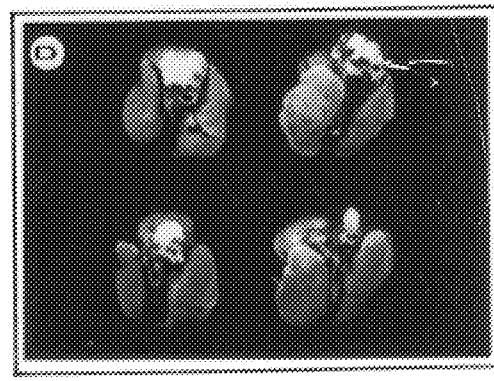
FIG. 1D is a photomicrograph of lungs of 1.0% MCP rats.

To more fully illustrate the present invention and referring to FIG. 1A of the drawings, rats were injected with $1 \times 10^6$ MLL cells in the hind limb on day 0. On day 4, when the primary tumors were approximately 1 $cm^3$ in size, 0.01%, 0.1%, or 1.0% (w:v) MCP was added to the drinking water of the rats (N=8 per group, experiments done twice) on a continuous basis. On day 14, the rats were anesthetized and the primary tumors were removed by amputating the hind limb. The addition of MCP to the drinking water did not affect primary tumor growth at any concentration (average tumor weight: control, 4.2±0.26 gm; 0.01%, 4.7±0.7 gm; 0.1%, 4.3±0.37 gm; 1.0%, 5.0±0.25 gm). Rats were then followed to day 30 when all groups were sacrificed and autopsied. Animals continuously ingested MCP in their drinking water during this period. Control and treated animals gained weight appropriately and there was no observable toxicity in the MCP treated animals. The lungs were removed, rinsed in water and fixed overnight in Bouin's Solution. The number of rats which suffered lung metastases was significantly reduced compared to control (15/16 rats with metastases) in the 0.1% ($P<0.03$) MCP (7/14 rats with metastases) ($p<0.001$) groups (FIG. 1A) rats consumed 30±4 ml of water per day in all groups. The number of MML tumor colonies were determined by counting under a dissection microscope. The lungs of the 1.0% MCP treated animals had on average significantly fewer metastatic colonies than control groups (9±4 in control compared to 1±1 in treated group ($p<0.05$) (FIG. 1B) (Mann-Whitney Test). The effect of MCP appeared to be dependent on its concentration in the drinking water. FIGS. 1C and 1D also depict lungs from tumor bearing animals (C-control, D-1.0% MCP) and highlights the effect of MCP on the reduction in number of the developed surface MLL lung colonies. 1% MCP also significantly reduced the number of animals with positive lymph node disease (55% in control, 13% in MCP treated, $p<0.01$). The treated animals suffered no apparent toxicity from MCP treatement. Animals gained weight at the same rate as controls. Daily water intake was 30±4 mls/rat in controls and treated groups. Hair texture, overall behavior, and stool color was unchanged.

Figure 2:
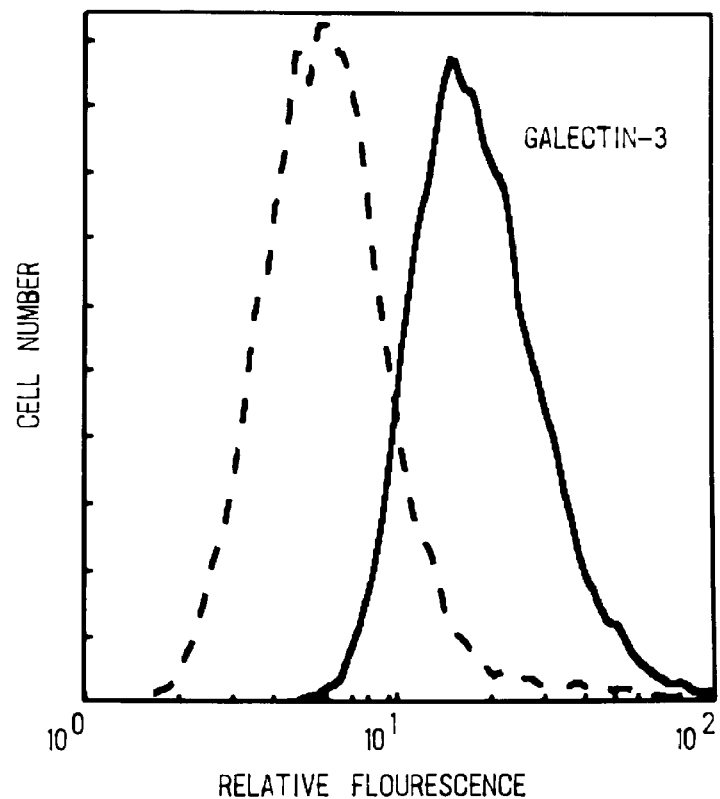
FIG. 2 is a plot of cell surface staining and western blot analysis (inset) for the expression of rat galectin-3 in MLL cells.

Since it had been previously demonstrated that MCP could interfere with cell-cell interactions mediated by cell surface carbohydrate-binding galectin-3 molecules, the question of whether MLL cells express galectin-3 was investigated. MLL cells, like many other cancer cells, express galectin-3 on their cell surface as determined by quantitative fluorescence flow cytometric analysis as shown in FIG. 2 and by immunoblotting of total cell extracted with mono-specific rabbit anti-galectin-3 peptide antibodies as shown in FIG. 2 (blot inset).

Tumor-endothelial cell adhesion is thought to be a key event in the metastatic process, and therefore, the effect of MCP on MLL-endothelial cell interaction was investigated. The adhesion of Cr-labeled MLL cells to confluent monolayers of rat aortic endothelial cells (RAEC) in the presence or absence of MCP is demonstrated in FIG. 3A. MCP was found to be a potent inhibitor of MLL cell adhesion to the endothelial cells FIGS. 3A and 3B.

Figure 3A:
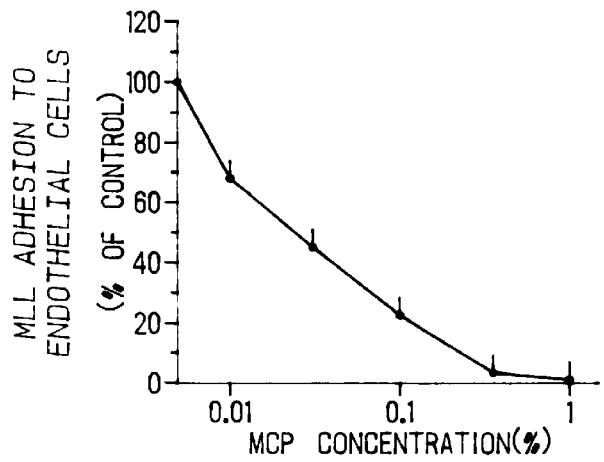
FIG. 3A is a graph which illustrates attachment of MLL cells in the absence or presence of various concentrations of MCP for 90 minutes at 4 C.
Figure 3B:
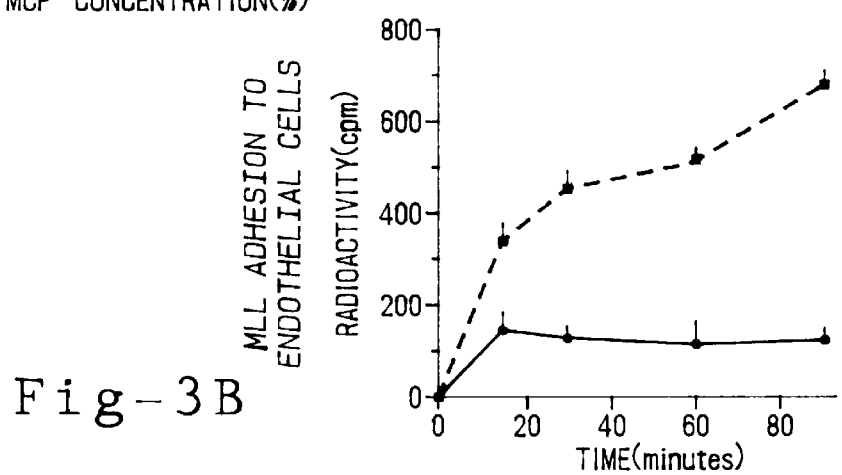
FIG. 3B is a graph which illustrates the time course for the attachment of MML cells to a confluent monolayer of RAEC In the absence (-----) or presence of 0.03% w/v MCP.
Figure 3C:
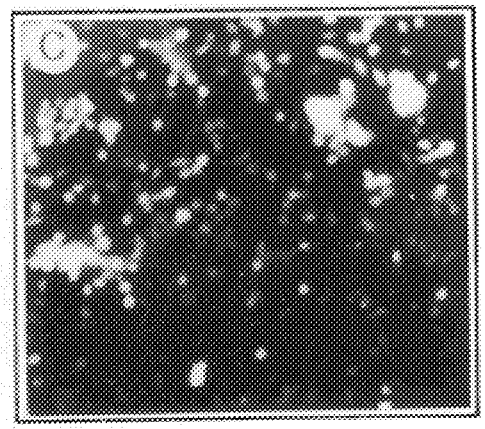
FIG. 3C is a photomicrograph of fluorescent MLL cell adhesion to RAEC cells in the absence of MCP.
Figure 3D:
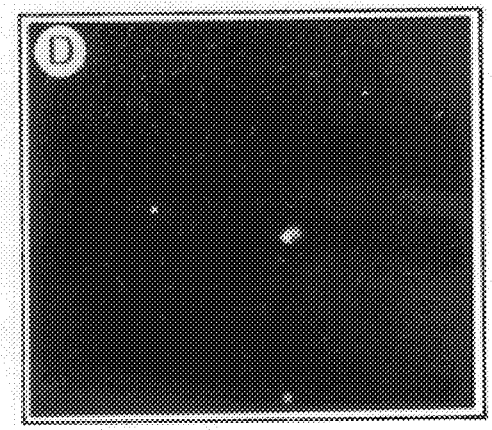
FIG. 3D is a photomicrograph of fluorescent MLL cell adhesion to RAEC cells in the presence of 0.1% w/v MCP.

MLL and RAEC cells were grown in RPMI 1640 media supplemented with 10% fetal bovine serum. RAEC were grown to confluence in tissue culture wells. $2.4 \times 10^6$ MLL cells were incubated for 30 minutes with 5 $\mu$Ci Na5$^1$CrO$_4$ at 37° C. in 2 ml serum free media with 0.5% bovine serum albumin. Following extensive washing $10^5$ MLL cells per well were then added to RAEC monolayers in quadruplicate. As seen in FIG. 3A, attachment of MLL cells in the absence or presence of various concentrations of MCP for 90 minutes at 4° C. was assessed. The cells were washed three times in cold phosphate-buffered saline to remove unbound cells. The cells were then solubilized with 0.1 NaOH for 30 minutes at 37° and the radioactivity was determined in a beta-counter. Each point represents the man of four wells and experiments were performed in duplicate. Bars represent standard error. As seen in FIG. 3B, time course for the attachment of MLL cells to a confluent monolayer of RAEC in the absence (-----) or presence of 0.03% (w/v) of MCP was determined. The presence of 0.03% MCP inhibited attachment of MLL cells to RAEC. Fluorescence MLL cell adhesion to RAEC $10^5$ MLL cells were incubated for 30 minutes in 0.1% FITC following extensive washing the cells were added to RAEC monolayers. Binding of MLL cells in the absence (FIG. 3C) or presence (FIG. 3D) of 0.1% (w/v) MCP (shown at ×160). It is apparent that MLL cells adhered rapidly to the RAEC monolayer, while only a limited degree of cell attachment was observed in the presence of MCP. Pictorial demonstration of the effect of MCP on the adhesion process is shown in FIG. 3C and FIG. 3D. MLL cells were fluorescently labeled in suspension with FITC, exposed to confluent monolayers of rat endothelial cells in 0.5% bovine serum albumin without (FIG. 3C) or with 0.1% MCP (FIG. 3D) for 60 min. The cultures were washed to remove the non-adherent cells and then photographed. In the non-treated cultures, the fluorescent MLL cells adhere almost uniformly bound to the endothelial monolayer (FIG. 3C) while in the presence of 0.1% MCP almost no fluorescent cells can be detected in association with the RAEC monolayer in the microscopic field (FIG. 3D).

The ability of cells to grow in semi-solid medium, i.e., anchorage-independence, may be used as a criterion for cell transformation and inhibition of such a process by drugs or antibodies is used to establish their efficacy. The growth of cells in a semi-solid medium requires that they migrate, invade, and establish new tumor foci in a process that appears to mimic many of the steps of in vivo metastasis. It has been previously suggested that the ability of tumor cells to interact with carbohydrate residues of glycoproteins via cell surface galectin-3 related to their ability to interact with the galactose residues of agarose (a polymer of D-galactose and L-anhydro-galactose) and to provide the minimal support needed for cell proliferation in this semi-solid medium. To this end it has been demonstrated that anti-galectin-3 monoclonal antibodies can inhibit the growth of tumor cells in agarose. Furthermore, transfection of normal mouse fibroblasts with the mouse galectin-3 cDNA results in the acquisition of anchorage-independent growth.

Figure 4A:
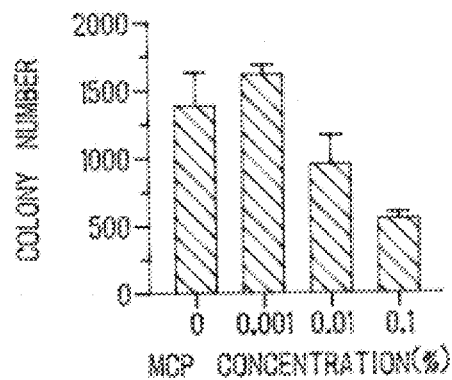
FIG. 4A is a chart which illustrates the effect of MCP on MLL colony formation in 0.5% agarose.
Figure 4B:
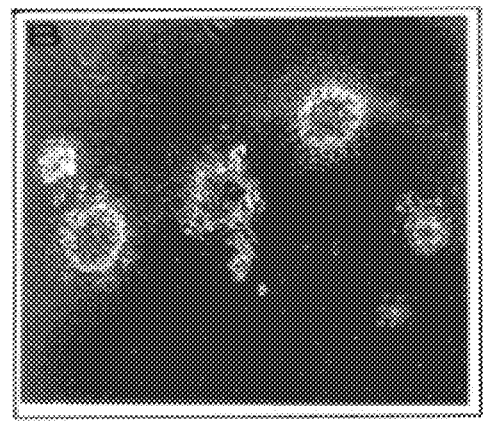
FIG. 4B is a phase contrast photomicrograph of MLL cells grown without MCP.
Figure 4C:
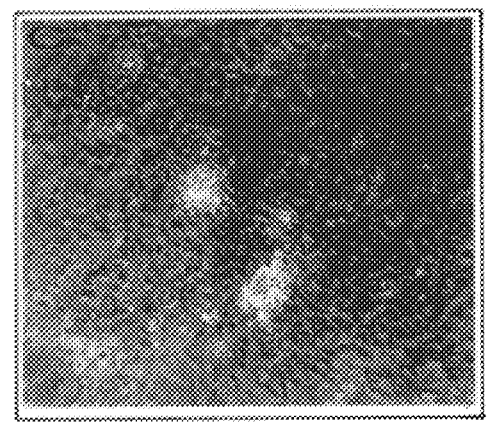
FIG. 4C is a phase contrast photomicrograph of MLL cells grown with 0.1% (w/v) MCP.

To determine the effect of MCP on MLL colony formation 0.5% agarose, MLL cells were detached from cultured monolayer with 0.02% EDTA in calcium and magnesium free (CMF)—PBS and suspended at $4 \times 10^3$ cells/ml in complete RPMI with or without MCP in varying concentrations. The cells were incubated for 30 minutes at 37° C. and them mixed 1:1 (vol/vol) with a solution of 1% agarose in RPMI 1:4 (vol/vol) preheated at 45° C. 2 ml aliquots of the mixture were placed on top of a precast layer of 1% agarose in 6 cm-diameter dishes. The cells were incubated for 8 days at 37° C., then fixed, counted and photographed. FIG. 4A illustrates the number of formed colonies was determined by a blinded observer using an inverted phase microscope. The presence of 0.1% MCP significantly inhibited the number of MLL colonies present to control (p<0.01 by Mann-Whitney). Bars represent the mean and S.E. of triplicate experiments. Phase contrast photomicrographs of MLL cells grown without (FIG. 4B) or with (FIG. 4C) 0.1% (w/v) MCP×160. As depicted in FIG. 4A, MCP inhibits MLL cell colony formation in agarose in a dose dependent manner. MCP inhibited both the number of MLL colonies and their size (FIGS. 4B and 4C). The inhibitory effect of MCP appears to be cytostatic rather than cytotoxic, since it has no effect on the rate of MLL cell growth in cultured monolayers in vitro (data not shown). MCP has similar effects o the ability of other tumor cells to form colonies in soft agar, including B16-F melanoma, UV-2237 fibrosarcoma, HT-1080 human fibrosarcoma, and A375 human melanoma. It is not known whether the MCP blocks the binding of the MLL cells to the galactose residues of agar, or competes with the binding of a carbohydrate-containing growth factor(s) with the cell surface galectin-3. Similarly, it is not known whether the MCP inhibition of tumor cell lung colony formation is vivo is mimicked by the inhibition of colony formation in vitro, although such a correlation appears to exist (FIG. 1 and FIG. 4).

Figure 5:
FIG. 5 is a photomicrograph of human primary prostatic adenocarcinoma tissue, illustrating the presence of Galectin-3.
Figure 6:
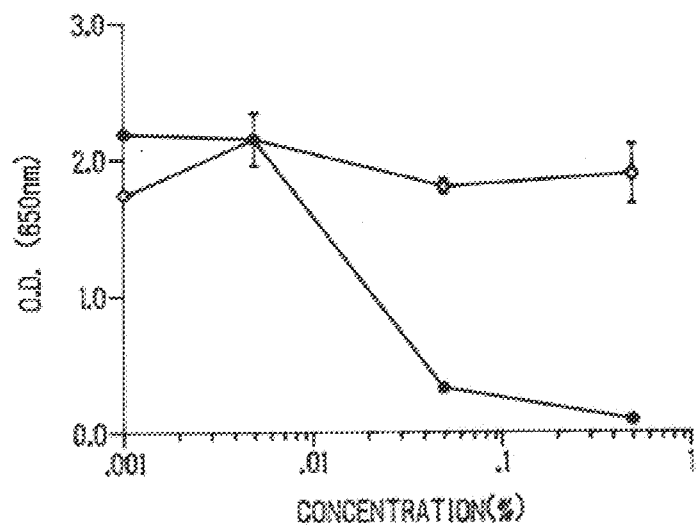
FIG. 6 is a graph illustrating the effects CP and MCP on B16F1 adhesion to laminin in the presence of varying concentrations of CP (0) or MCP (●). Vertical bars show mean ± standard deviation computed from the t distribution of the mean.
Figure 7A:
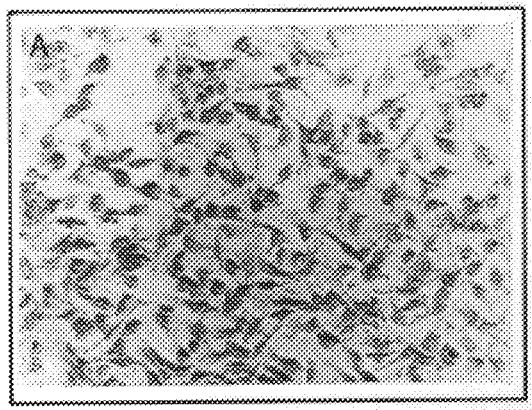
FIG. 7A is a phase-contrast photomicrograph of B16F1 cells plated on laminin. The cells were cultured in DMEM alone.
Figure 7B:
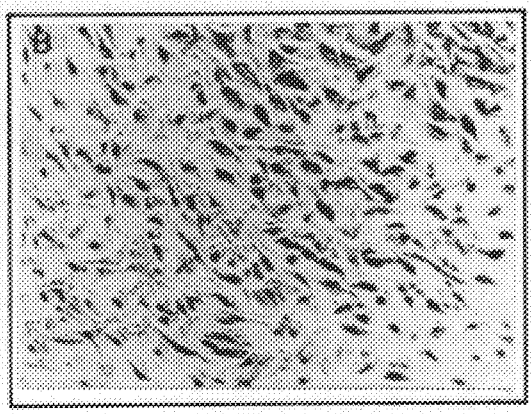
FIG. 7B is a phase-contrast photomicrograph of B16F1 cells plated on laminin cultured in the presence of 0.5% CP and DMEM.
Figure 7C:
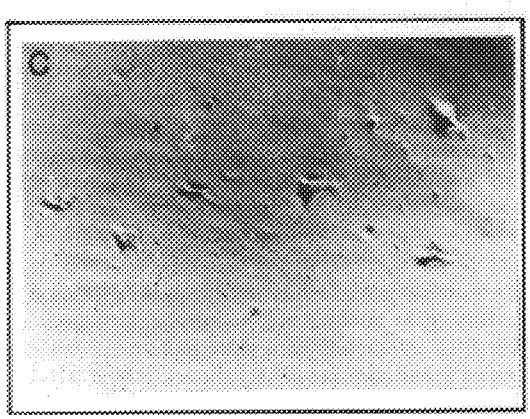
FIG. 7C is a phase-contrast photomicrograph of B16F1 cells plated on laminin cultured in the presence of 0.5% MCP and DMEM.
Figure 8:
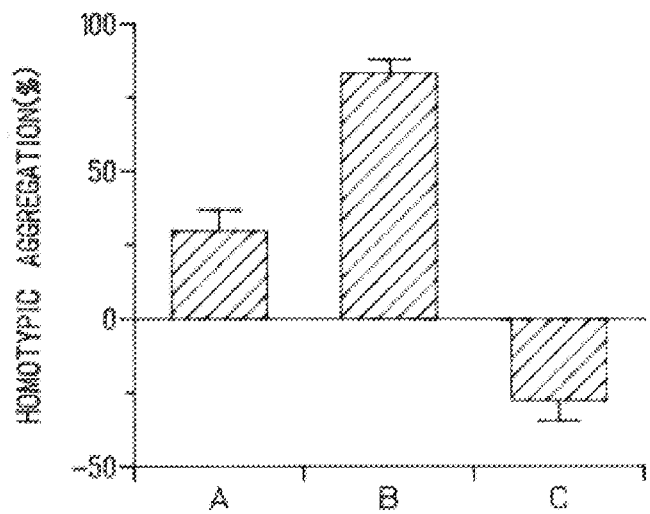
FIG. 8 is a chart illustrating the effects of CP and MCP on asialofetuin-induced homotypic aggregation in the presence of 20 μg/ml asialofetuin alone (A) or with added 0.5% CP (B) or 0.5% MCP (C). Vertical bars show mean standard deviation computed from the t-distribution of the mean.
Figure 9A:
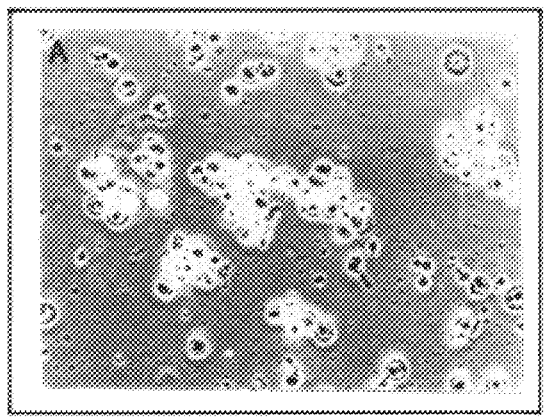
FIG. 9A is a phase-contrast photomicrograph of homotypic aggregation of B16-F1 cells in the presence of 20 μg/ml asialofetuin alone.
Figure 9B:
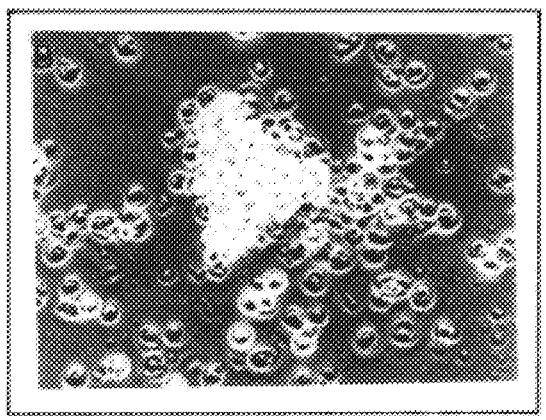
FIG. 9B is a phase-contrast photomicrograph of homotypic aggregation of B16-F2 cells in the presence of 0.5% CP and asialofetuin.
Figure 9C:
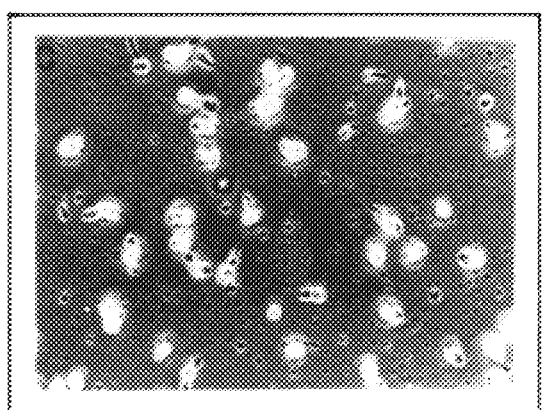
FIG. 9C is a phase-contrast photomicrograph of homotypic aggregation of B16-F2 cells in the presence of 0.5% MCP and asialofetuin.
Figure 10:
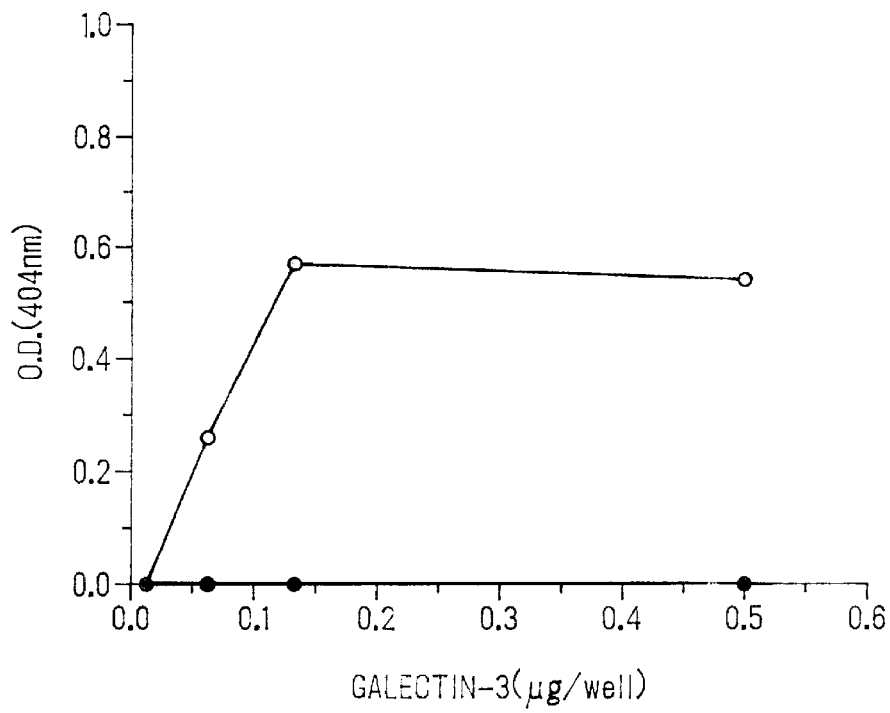
FIG. 10 is a graph illustrating the binding of galectin-3 to MCP coated wells.

The results presented here provide a new, nontoxic, oral method to prevent spontaneous prostate cancer metastasis. In preliminary experiments, we have found that galectin-3 is present in human prostate cancer pathologic tissue specimens as well as the human prostate adenocarcinoma cell line PC-3. For immunohistochemistry, 5 $\mu$m formalin fixed paraffin embedded primary prostatic adenocarcinoma sections were deparaffinized, rehydrated and microwaved (medium - high) for 10 minutes in 1 mM sodium citrate buffer. After washing in PBS sections were blocked in normal goat serum for 30 minutes, and then incubated with the primary antibody rat anti-galectin-3-TIB-166 monoclonal antibody. Sections were then washed within DPBS for 30 minutes and then incubated with biotinylated anti-rat IgG, washed, and incubated with avidin-biotinylated horse radish peroxidase followed by a peroxidase substrate 3'-3'-diaminobenzidine. Sections were counterstained with 3% methyl green and mounted with gelatin-glycerin. The section demonstrated in FIG. 5 is from a patient with invasive prostate cancer. PC-3 cell extract was immunoblotted and analyzed for the presence of human galectin-3 as described in the legend to FIG. 2. The expression of galectin-3 in specimens of human prostate was examined by immunohistochemistry with T1B-

166 anti-galectin-3 monoclonal antibodies. The galectin-3 was mainly expressed in the prostate carcinoma cells with little stromal staining and variable normal epithelial staining (FIG. 5). Galectin-3 staining with this antibody was associated with intense nuclear, cytoplasmic, and cell surface staining. Further investigations will determine the role of galectin-3 in normal and cancerous prostate tissue as well as the ability of MCP to inhibit human prostate metastasis in nude mice. MCP molecules appear to be absorbed into the blood stream after oral administration and compete with the natural ligand(s) recognition of tumor cell surface galectins essential for the successful establishment of secondary tumor cell colonies. Further work is underway to characterize the active moieties of MCP as well as their serum levels since little is known about the molecular features of the pectins. It appears that the effect of MCP is in the early stages of metastasis, possibly inhibiting the formation of tumor cell emboli as well as inhibiting the interaction of cancer cells with the endothelium of target organ, rather than late events such as metastatic cell growth since MCP has no effect on MLL primary tumor growth or angiogenesis.

Since natural citrus pectin (CP) and pH-modified citrus pectin (MCP) are highly branched and non-branched complex polysaccharides, respectively, rich in galactoside residues, capable of binding to the carbohydrate-binding domain of galectin-3, we studied the effects of CP and MCP on cell-cell and cell-matrix interactions mediated by carbohydrate-recognition. MCP, but not CP, inhibited B16-F1 melanoma cells adhesion to laminin and asialofetuin-induced homotypic aggregation. Both MCP and CP inhibited anchorage-independent growth of B16-F1 cells in semisolid medium, ie., agarose. These results indicate that carbohydrate-recognition by cell surface galectin-3 may be involved in cell-extracellular matrix interaction and play a role in anchorage-independent growth as well as the in vivo embolization of tumor cells.

More specifically, endogenous vertebrate galactoside-binding lectins have been identified and characterized in a diversity of tissues and cells. The lectins are divided into two abundant classes based on their sizes, the molecular masses of which are ~14 kDa and ~30 kDa that have been recently designated as galectin-1 and galectin-3, respectively. Galectin-3 represents a wide range of molecules i.e., the murine 34 kDa (mL-34) and human 31 kDa (hL-31) tumor-associated galactoside-binding lectins, the 35 kDa fibroblast carbohydrate-binding protein (CBP35), the IgE-binding protein (εBP), the 32 kDa macrophage non-integrin laminin-binding protein (Mac-2), and the rat, mouse, and human forms of the 29 kDa galactoside-binding lectin (L-29). Molecular cloning studies have revealed that the polypeptides are identical. The galectin-3 contain two structural domains, an amino-terminal domain containing a collagen-like sequence and globular carboxy-terminal domain encompassing the galactoside-binding site. Whether all of the above-mentioned galactoside-biding lectins share the same natural ligand(s) is not yet known. Although galectin-3 has been considered to be an S-type lectin that requires reducing conditions for its carbohydrate-binding activity, recent studies have produced evidence to the contrary. Several lines of analysis have demonstrated that the galectins participate in cell-cell and cell-matrix interactions by recognizing and binding complementary glycoconjugates and thereby play a crucial role in various normal and pathological processes.

Galectin-3 is highly expressed by activated macrophages and oncogenically transformed and metastatic cells. Elevated expression of the polypeptide is associated with an increased capacity for anchorage-independent growth, homotypic aggregation, and tumor cell lung colonization, which suggests that galectin-3 promotes tumor cell embolization in the circulation and enhances metastasis. We have previously reported that intravenous injection of CP increases lung colonization of the B16-F1 murine melanoma cells, while MCP decreases lung colonization. Although the increased lung colonization by CP is most probably due to its ability to promote homotypic aggregation, the mechanism by which MCP prevents the lung colonization remains less well established.

Laminin, the major non-collagenous component of basement membranes, is an N-linked glycoprotein carrying poly-N-acetyllactosamine sequences, and is implicated in cell adhesion, migration, growth, differentiation, invasion and metastasis. Galectins which bind with high affinity to oligosaccharides containing poly-N-acetyllactosamine sequences also bind to the carbohydrate side chains of laminin in a specific sugar-dependent manner.

In order to further study the functional properties of galectin-3, we utilized CP and MCP, and examined whether they would affect galectin-3 -related properties of B16-F1 murine melanoma cells. We have found that: (a) MCP, but not CP, inhibits cell adhesion to laminin; (b) MPC inhibits asialofetuin-induced homotypic aggregation, while CP enhances it; and (c) both CP and MCP inhibit anchorage-independent growth in semi-solid medium.

CP and EHS laminin were purchased from Sigma, St. Louis, Mo. MCP was prepared from CP by pH modification according to the above-described procedure of Albersheim et al. Asialofetuin was prepared by mild acid hydrolysis of fetuin (Spiro method; Grand Island Biological Co., Grand Island, N.Y.) in 0.05M $H_2S)_4$ at 80° C. for 1 h. Recombinant galectin-3 was extracted from bacteria cells by single-step purification through an asialofetuin affinity column as described elsewhere. Recombinant galectin-3 eluted by lactose was extensively dialyzed against CMF-PBS before use. Anti-galectin-3 monoclonal antibody was obtained from Dr. R. Lotan, University of Texas, M. D. Anderson. Horseradish peroxidase (HRP)- conjugated rabbit anti-rat IgG+IgM and 2, 2'-azino-di(3-ethylbenzthiazoline sulfonic acid) (ABTS) substrate kit were purchased from Zymed, South San Francisco, Calif. B16-F1 murine melanoma cells were cultured in Dulbecco's modified Eagles' minimal essential medium (DMEM) supplemented with 10% heat-inactivated fetal bovine serum, non-essential amino acids, 2 MM glutamine, and antibiotics. The cells were maintained at 37° C. in a humidified atmosphere of 7% $CO_2$ and 93% air.

Cell adhesion to laminin—Tissue culture wells of 96-well plates were precoated overnight at 4° C. with EHS laminin (2 μg/well) in $CA^{2+}$- and $Mg^{2+}$-free phosphate-buffered saline, pH 7.2 (CMF-PBS), and the remaining protein binding sites were blocked for 2 h at room temperature with 1% bovine serum albumin (BSA) in CMF-PBS. Cells were harvested with 0.02% EDTA in CMF-PBS and suspended with serum-free DMEM. $5 \times 10^4$ cells were added to each well in DMEM with or with CP or MCP of varying concentrations. After incubation for 2 h 15 37° C., non-adherent cells were washed off with CMF-PBS. Adherent cells were fixed with methanol and photographed. The relative number of adherent cells was determined in accordance with the procedure of Olier et al. Briefly, the cells were stained with methylene blue followed by the addition of HCl-ethanol to release the dye. The optical density (650 nm) was measured by a plate reader.

Asialofetuin-induced homotypic aggregation—Cells were detached with 0.02% EDTA In CMF-PBS and suspended at $1\times10^6$ cell/ml in CMF-PBS with or without 20 µg/ml of asialofetuin and 0.5% CP or 0.5% MCP. Aliquots containing 0.5 ml of cell suspension were placed in siliconized glass tubes and agitated at 80 rpm for 60 minutes at 37° C. The aggregation was then terminated by fixing the cells with 1% formaldehyde in CMF-PBS. Samples were used for counting the number of single cells, and the resulting aggregation was calculated according to the following equation: $(1-Nt/Nc)\times100$, where Nt and Nc represent the number of single cells in the presence of the tested compounds and that in the control buffer (CMF-PBS), respectively.

Galectin-3 binding to MCP—96-well plates were coated with CMF-PBS containing 0.5% MCP and 1% BSA and dried overnight. Recombinant galectin-3 serially diluted in CMF-PBS containing 0.5% BSA and 0.05% Tween-20 (solution A) in the presence or absence of 50 mM lactose was added and incubated for 120 minutes, after which the wells were drained and washed with CMF-PBS containing 0.1% BSA and 0.05% Tween-20 (solution B). Rat anti-galectin-3 in solution A was added and incubated for 60 minutes, followed by washing with solution B and incubation with HRP-conjugated rabbit anti-rat lgG_1 gM in solution A for 30 minutes. After washing, relative amounts of bound enzyme conjugated in each well were ascertained by addition of ABTS. The extent of hydrolysis was measured at 405 nm.

Colony formation in semi-solid medium—Cells were detached with 0.02% EDTA in CMF-PBS and suspended at $1\times10^3$ cell/ml in complete DMEM with or without CP or MCP of varying concentrations. The cells were incubated for 30 min at 37° C. and then mixed 1:1 (vol/vol) with a solution of 1% agarose in distilled water-complete DMEM (1:4, vol/vol) preheated at 45° C. 2 ml aliquots of the mixture were placed on top of a precast layer of 1% agarose in 6 cm-diameter dishes. The cells were incubated for 14 days at 37° C., and the number of formed colonies was determined using an inverted phase microscope after the fixation by the addition of 2.6% glutaraldehyde in CMF-PBS.

It was previously shown that laminin can serve as a ligand for soluble galectin-3 and the B16-F1 cells express galectin-3 molecules on their cell surface. These results together with the effects of CP and MCP on the lung colonization of i.v. injected B16-F1 cells prompted us to initially examine their effects on B16-F1 cell adhesion to laminin in order to evaluate the possible role of cell surface galectin-3 in such a process. As shown in FIGS. 6 and 7A–C, MCP significantly inhibited cell adhesion to laminin in a dose-dependent manner, while CP had no apparent effect on either cell binding or spreading onto laminin. The simple sugar inhibitor of galectin-3 lactose, did not inhibit cell adhesion to laminin at concentrations as high as 100 mM (data not shown). Competitive binding assay utilizing soluble recombinant galectin-3 failed to block cell adhesion to laminin and the anti-Mac-2 monoclonal antibodies failed in this regard as well (data not shown), suggesting that the inhibitory effect of MCP cannot be attributed solely to its interruption of the interaction between galectin-3 and N-acetyllactosaminyl side chains on laminin since cells may utilize the integrins for binding to the protein core of laminin. Furthermore, the anti-Mac-2 monoclonal antibody is not directed against the carbohydrate-binding domain of galectin-3 but rather to its N-terminal, thus, the exact mechanism by which MCP blocks adhesion, in contrast to CP and lactose, remains unclear. The inhibitory effect of MCP is not due to cytotoxicity, because MCP (0.5%) did not affect either viability or in vitro growth of the cells.

A good correlation has been established between the propensity of tumor cells to undergo homotypic aggregation in vitro and their metastatic potential in vivo. B16 melanoma cell clumps produce more lung colonies after i.v. injection than do single cells. Moreover, anti-galectin-3 antibody has been shown to inhibit asialofetuin-induced homotypic aggregation (14), suggesting that the cell surface galectin-3 polypeptides bring about the formation of homotypic aggregates following their interaction with the side chains of glycoproteins. As shown in FIGS. 8 and 9A–C, MCP significantly reduced the formation of homotypic aggregates, while CP enhanced it. Most probably the non-branched MCP mimics the behavior of the specific sugar inhibitor, i.e., lactose, such that it masks the interaction of the cell surface galectin-3 molecules with galactoside residues of asialofetuin, resulting in a reduced homotypic aggregation. Conversely, it is conceivable to assume that the structural characteristic of a branched carbohydrate polymer allows CP to serve as a cross-linker bridge between adjacent cells, leading to the enhanced formation of homotypic aggregates. Taken together, it may be suggested that MCP could prevent metastasis by disrupting cell-cell and cell-matrix interactions that are crucial for tumor cells to form metastatic lesions.

The aforementioned effects of MCP to inhibit B16-F1 cell adhesion to laminin and homotypic aggregation may be due to its interaction with galectin-3 on the cell surface, because CP has been previously shown to bind B16-F1 cell surface in a lactose-dependent manner. To address the binding of galectin-3 to MCP, we employed an enzyme-linked immunosorbent assay where we found that recombinant galectin-3 bound immobilized MCP in a dose-dependent manner and the binding was completely blocked by lactose (FIG. 9). These results allow us to attribute the inhibitory effects of MCP on homotypic aggregation to its binding to cell surface galectin-3 molecules. On the other hand, we do not know how MCP, but not CP, impairs B16-F1 cell adhesion to laminin. Since pH modification of CP, which is a branched complex polysaccharide polymer, results in the generation of non-branched carbohydrate chains of the same sugar composition, it is likely that MCP binds more avidly to the cell surface galectin-3 molecules than does CP. Taken together with the fact that anti-integrin antibodies inhibit murine B16 melanoma cell attachment to laminin substrates, we presume that MCP sterically inhibits laminin recognition by the integrin class of laminin receptors, or that the interaction of cell surface galectin-3 with poly-N-acetyllactosamine sequences on laminin may act in concert with integrins for cell adhesion to laminin. The possibility that the interaction of MCP with galectin-1 having the same sugar specificity as galectin-3 might affect its processes to impair B16-F1 cell adhesion to laminin and homotypic aggregation can be most probably ruled out since galectin-1 is a secreted protein.

Figure 11:
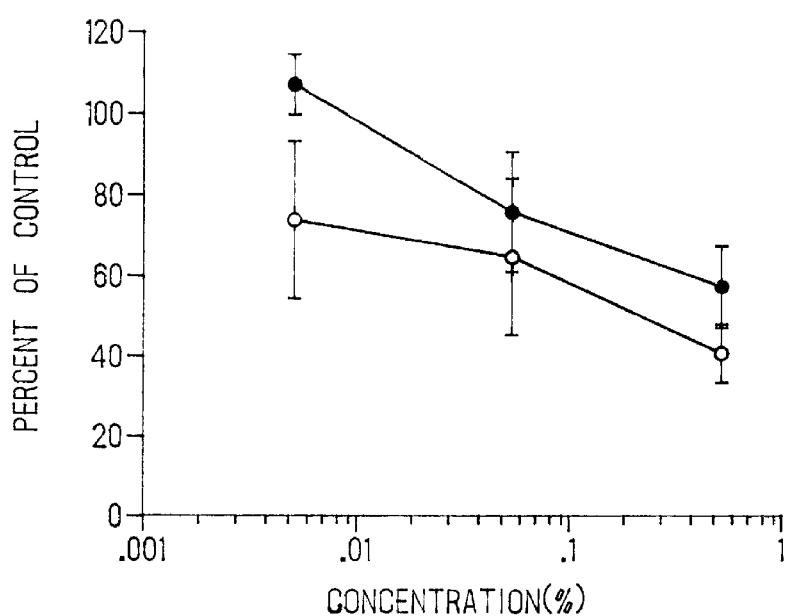
FIG. 11 is a graph illustrating the effects of CP and MCP on the ability of B16F1 cells to form colonies in 0.5% agarose (CP 0 MCP ●).

The ability of cells to grow in semi-solid medium, i.e., "anchorage independence" is used as a criterion for cell transformation, because this property is usually exhibited only by transformed and tumorigenic cells. Previously it has been suggested that the ability of tumor cells to interact with glycoprotein carbohydrate residues via cell surface galectin-3 is related to their ability to interact with the galactose residues of agarose (a polymer of D-galactose and L-anhydrogalactose) and to the efficiency of colony formation in this semi-solid medium. It has been also shown that anti-galectin-3 monoclonal antibodies inhibit growth of tumor cells in agarose and that there is an inverse relationship between the expression of galectin-3 and the suppression of the transformed phenotype. Transfection of normal mouse fibroblast with the mouse galectin-3 cDNA results in the acquisition of anchorage-independent growth properties. To further verify the possibility that cell surface galectin-3 play a key role for cells to grow in semi-solid medium, we examined the effects of CP and MCP on anchorage-independent growth of B16-F1 melanoma cells. As shown in FIG. 11, CP and MCP inhibited the growth of B16-F1 cell colonies in the semi-solid matrix in a dose-dependent manner. Similarly, lactose inhibited anchorage-independent growth in a dose-dependent manner as well (data not shown). The dose-dependent inhibitory effect of CP and MCP was not restricted to B16-F1 melanoma cells. The growth in soft agar of UV-2237-10-3 murine fibrosarcoma cells, HT1080 human fibrosarcoma cells, and A375C1.49 human melanoma cells was also equally inhibited. It is possible that the soluble CP and MCP compete with the galactose residues of agarose for galectin-3 binding, leading to apparent growth inhibition by depriving the cells of the minimal support of the matrix required for cell proliferation. It also may be argued that CP and MCP as well as the anti-galectin-3 antibodies possibly behave like an antagonist of an as-yet unrecognized glycoconjugate growth factor which interacts with galectin-3, or they sterically hinder the access of known growth factors to the membrane receptors. However, the fact that in vitro anchorage-dependent growth and tumorigenicity of B16-F1 cells in syngenic mice were not impaired by MCP (0.5%) plausibly enables us to rule out the aforementioned possibilities. Since the ability of cells to grow in semi-solid medium is used as a criterion for cell transformation, the acquisition of cell surface galectin-3 might be an early step of the post-transformed cascade.

What is claimed is:

1. A method for the therapeutic treatment of cancer in mammals comprising orally administering a therapeutically effective amount of pH modified pectin to a mammal afflicted with cancer, wherein said cancer is prostate cancer.

2. A method for the therapeutic treatment of cancer in mammals comprising orally administering a therapeutically effective amount of pH modified pectin to a mammal afflicted with cancer, wherein said cancer is human prostate cancer.

* * * * *